United States Patent [19]

Poretz et al.

[11] Patent Number: 5,599,831

[45] Date of Patent: Feb. 4, 1997

[54] METHOD OF PREPARATION OF PHARMACEUTICAL COMPOSITIONS

[76] Inventors: Ronald D. Poretz, 8 York Rd., Marlboro, N.J. 07746; Simon A. Chernomorsky, 23 Valley Forge La., Morris Plains, N.J. 07950

[21] Appl. No.: 250,222

[22] Filed: May 27, 1994

[51] Int. Cl.⁶ .......................... A01N 43/38; A01N 55/02; C07K 1/00; C07B 47/00
[52] U.S. Cl. .......................... 514/410; 514/185; 424/450; 530/359; 540/145
[58] Field of Search .......................... 424/450; 530/359; 604/20; 540/145; 514/185, 410

[56] References Cited

U.S. PATENT DOCUMENTS

| | | | |
|---|---|---|---|
| 4,603,209 | 7/1986 | Tsien et al. | 436/173 |
| 5,028,594 | 7/1991 | Carson | 514/23 |
| 5,049,390 | 9/1991 | Wojdani | 424/450 |
| 5,093,349 | 3/1992 | Pandey et al. | 540/145 |
| 5,166,197 | 11/1992 | Kenney et al. | 540/128 |
| 5,169,944 | 12/1992 | Nelson et al. | 436/173 |
| 5,173,504 | 12/1992 | Dougherty | 514/410 |
| 5,177,073 | 1/1993 | Gulliya et al. | 424/484 |
| 5,198,460 | 3/1993 | Pandey et al. | 514/410 |
| 5,214,036 | 5/1993 | Allison et al. | 514/185 |
| 5,238,940 | 8/1993 | Liu et al. | 514/410 |
| 5,244,671 | 9/1993 | Vogel et al. | 424/450 |
| 5,257,970 | 11/1993 | Dougherty | 424/450 |
| 5,258,453 | 11/1993 | Kopecek et al. | 525/54.1 |
| 5,308,861 | 5/1994 | Aizawa et al. | 514/410 |
| 5,419,760 | 5/1995 | Narciso, Jr. | 604/8 |

OTHER PUBLICATIONS

R. Pottier, and J. C. Kennedy, "The possible role of ionic species in selective biodistribution of photochemotherapeutic agents toward neoplastic tissue," *J. Photochem. Photobiol. B. Biol.*, 8, 1–16 (1990).

A. B. A. Jansen and T. J. Russell, "Some novel penicillin derivatives", *J. Chem. Soc.*, 1965, 2127–2132 (1965); H. Ferres, Pro-drugs of β-lactam antibiotics, *Chem. Ind.*, 435–440 (1980).

R. Y. Tsien, "A non-disruptive technique for loading calcium buffers into cells", *Nature*, 290, 527–528 (1981).

S. A. Chernomorsky, C. Wong and R. D. Poretz, "Pheophorbide α–induced photo-oxidation of cytochrome c: implication for photodynamic therapy", *Photochem. Photobiol* 55, 205–211 (1992).

H. Ferres, "Pro-drugs of β-lactam antibiotics," *Chem. Ind.*, 435–440 (1980).

L. C. Bergstrom, I. Vucenik, S. Chernomorsky and R. D. Poretz, "Targeted photoactive immunoliposomes are cytotoxic to human bladder carcinoma cells," *FASEB J.*, 5, A1558, (1991).

J. D. Spikes, "Chlorins as photosensitizers in biology and medicine," *J. Photochem. Photobiol. B. Biol.*, 6, 259–274 (1990).

(List continued on next page.)

*Primary Examiner*—John Kight
*Assistant Examiner*—Louise Leary
*Attorney, Agent, or Firm*—Skadden, Arps, Slate, Meagher & Flom

[57] ABSTRACT

A method of preparing a pharmaceutically beneficial, pH-sensitive amphipathic drug compound is disclosed. The pH-sensitive amphipathic parent drug compound is converted to a lipophilic derivative which is then combined with a lipophilic carrier for delivery to the lysosomes of target cells. The lipophilic derivative of the parent compound is acted upon by lysosomal enzymes to yield the parent compound. The method is demonstrated for pharmaceutically beneficial porphyrins that may be used as photosensitizers in photodynamic therapy (PDT). In particular, the method is demonstrated for the esterification of chlorin $e_6$ and pheophorbide a for the photocytotoxic treatment of human bladder tumor cells.

31 Claims, 2 Drawing Sheets

OTHER PUBLICATIONS

S. A. Chernomorsky, R. D. Poretz and A. B. Segelman, "The photodynamic effect of chlorophyll derivatives on murine myeloma cells in tissue culture," *Photochem. Photobiol.*, 39, 49S (1984).

A. B. Segelman, I. K. Hagen, S. A. Chernomorsky, K. Weadock and G. H. Sigel, Jr., "Highly purified pheophorbide α as a photosensitizer in human bladder cancer in vitro," *New Directions of Photodynamic Therapy*, (Edited by D. C. Neckers), pp. 205–209, SPIE (1987).

G. A. Kostenich, I. N. Zhuravkin, A. V. Furmanchuk and E. A. Zhavrid, "Photodynamic therapy with chlorin $e_6$. A morphologic study of tumor damage efficiency in experiment," *J. Photochem. Photobiol. B. Biol.*, 11, 307–318 (1991).

A. R. Oseroff, D. Ohuoha, T. Hasan, J. C. Bommer and M. L. Yarmush "Antibody targeted photolysis: selective photodestruction of human T-cell leukemia cells using monoclonal antibody–chlorin $e_6$ conjugates," *Proc. Natl. Acad. Sci. USA*, 83, 8744–8748 (1986).

T. V. Akhlynina, P. V. Gulak, N. V. Serebryakova, A. A. Rosenkranz and A. S. Sobolev "Photodynamic action of concanavalin A–Chlorin $e_6$ conjugate on human fibroblasts," *Byull. Eksp. Biol. Med.*, 109, 183–184 (1990).

J. Kopecek, N. L. Krinick, B. Rihova and K. Ulbrich "Targetable N–(2-hydroxypropyl) methacrylamide copolymer–chlorin $e_6$ conjugates," *Photodynamic Therapy: Mechanism II*, (Edited by T. J. Dogherty), pp. 144–152, SPIE, (1990).

R. Bachor, C. R. Shea, S. J. Belmonte and T. Hasen "Free and conjugated chlorin $e_6$ in the photodynamic therapy of human bladder carcinoma cells," *J. Urol.*, 146, 1654–1658 (1991).

R. Bachor, M. Scholz, C. R. Shea and T. Hasan, "Mechanism of photosensitization by microsphere-bound chlorin $e_6$ in human bladder carcinoma cells," *Cancer Res.*, 51, 4410–4414 (1991).

A. S. Sobolev, T. V. Akhlynina, S. V. Yachmenev, A. A. Rosenkranz and E. S. Severin, "Internalizable insulin–BSA–chlorin $e_6$ conjugate is a more effective photosensitizer than chlorin $e_6$ alone," *Biochem. Int.*, 26, 445–450 (1992).

D. Sahai, J–L. Lo, I. K. Hagen, L. Berstrom, S. Chernomorsky and R. D. Poretz, "Metabolically convertible lipophilic derivatives of pH–sensitive amphiphatic photosensitizers," *Photochem. and Photobiol.*, 58, pp. 803–808 (1993).

F. N. Jiang, B. Allison, D. Liu and J. G. Levy, "Enhanced photodynamic killing of target cells by either monoclonal-antibody or low–density–lipoprotein mediated delivery systems," *Controll. Release*, 19, 41–58 (1992).

M. Zapata, A. M. Ayala, J. M. Franco and J. L. Garrido, "Separartion of chlorophylls and their degradation products in marine phytoplankton by reversed–phase high–performance liquid chromatography," *Chromatographia*, 23, 26–30 (1987).

G. W. Kenner, S. W. McCombie and K. M. Smith, "Pyrroles and related compounds. Part XXIV. Separation and oxidative degradation of chlorophyll derivatives," *J.C.S. Perkin I*, 2517–23 (1973).

J. H. Furhop and K. M. Smith, "Laboratory methods," *Porphyrins and Metalloporphyrins*, (Edited by K. M. Smith), Elsevier, Amsterdam, pp. 774–775 (1975).

L. C. Bergstrom, I. Vucenik, I. K. Hagen, S. A. Chernomorsky and R. D. Poretz, *J. Photochem. Photobiol.*, in press (1994).

R. D. Poretz, I. Vucenik, L. Bergstrom, A. Segelman, G. Sigel Jr. and S. A. Chernomorsky, SPIE 1065, 97–203 (1989).

METHOD OF PREPARATION OF PHARMACEUTICAL COMPOSITIONS

FIELD OF INVENTION

This invention relates to a method of delivering a pH-sensitive amphipathic drug compound to a patient. More specifically, the subject method relates to the preparation of a lipophilic derivative of a pH-sensitive amphipathic compound that may be delivered to target cells of a patient by a lipophilic carrier or other pharmaceutically acceptable agent and then converted to its pharmaceutically beneficial, pH-sensitive amphipathic form by lysosomal enzymes.

BACKGROUND OF THE INVENTION

An approach utilized in drug therapy is to employ delivery vehicles which exhibit pharmaceutically protective or specific targeting properties. Vehicles such as liposomes, immunoliposomes and lipoproteins are capable of binding lipophilic pharmaceuticals and facilitating their cellular uptake by endocytosis leading to delivery of the pharmaceutical to lysosomes of target cells.

Presently, drugs that are designed to be lipophilic and compatible with lipophilic carriers capable of delivering the drug to cells by endocytosis do not have characteristics that allow them to reach other cellular compartments. Accordingly, a drug having sites of action in cellular compartments other than in lysosomes cannot be effectively delivered by lipophilic carriers to target cells by endocytosis with the degree of selectivity that may be desired. A need exists for a pharmaceutical that undergoes intracellular redistribution throughout a target cell after the pharmaceutical is preferentially delivered to the lysosome of that cell.

Selective photocytotoxicity is the basis of photodynamic therapy (PDT). The PDT process requires photosensitizers (PS) that exhibit high selectivity and effective photoactivity at wavelengths suitable for significant tissue penetration. The first generation drug for PDT, hematoporphyrin derivative (HpD), shows considerable cross sensitization with non-target tissues and has absorption properties that require the use of light at wavelengths exhibiting only moderate tissue penetration. In an effort to improve upon the photoactive properties and the tissue selectivity of potentially useful PDT systems, attempts have been made to treat the elements of selectivity and photoactivity separately. Approaches have included the use of PS associated with liposomes and low-density lipoprotein (LDL). These avenues are premised, in part, on the initial use of the normal cellular mechanism of receptor-mediated endocytosis to direct the internalized material, through vesicular transport, to the lysosome. The endolysosomal compartments are acidic (~pH 4.8–6.5) and contain a host of hydrolytic enzymes. Lysosomal targeting of a PS has resulted in phototoxic responses in target cells under conditions wherein the PS is solely, or predominantly in the lysosomes. Damage to virtually all cellular compartments, however, has been implicated with photocytotoxicity in PDT. Accordingly, these results suggest that multi-site photodamage to a target cell, following delivery of the photosensitizer to the cell, may be an important mechanism that could facilitate cytotoxicity.

To design potentially useful PS applicable for lysosomal-targeted PDT that will allow a multisite response, it has been proposed to use pH-sensitive amphipathic PS, S. A. Chernomorsky, C. Wong and R. D. Poretz, "Pheophorbide a-induced photo-oxidation of cytochrome c: implication for photodynamic therapy", Photochem. Photobiol 55, 205–211 (1992). Such PS compounds exhibit a tendency to preferentially partition, depending upon the pH of the environment, into lipophilic membranes or into an aqueous milieu. Such compounds, when delivered to the acidic lysosome, are relatively hydrophobic and tend to diffuse into the organelle membrane. Contact with the neutral pH of the adjacent cytosol, however, will result in conversion of the photosensitizer to a more hydrophilic anionic species, allowing for it to diffuse into that compartment and partition throughout the lipophilic and aqueous compartments of the cell.

A concern with pH-sensitive amphipathic compounds that are wedded to a lipophilic carrier, such as liposomes or LDL, is the potential tendency of such substances to partition out of the lipophilic carrier into more hydrophilic compartments prior to delivery into the cell, R. Pottier, and J. C. Kennedy, "The possible role of ionic species in selective biodistribution of photochemotherapeutic agents toward neoplastic tissue," J. Photochem. Photobiol. B. Biol., 8, 1–16 (1990).

Acyloxyalkyl esters of hydrophilic drugs have been utilized to enhance intestinal uptake of orally delivered pro-drugs, with the resulting enzymatic de-esterification yielding the more hydrophilic drug, A. B. A. Jansen and T. J. Russell, "Some novel penicillin derivatives", J. Chem. Soc., 1965, 2127–2132 (1965); H. Ferres, "Pro-drugs of β-lactam antibiotics," Chem. Ind., 435–440 (1980).

Similarly, Tsien has employed acetoxymethyl esters of fluorescent compounds to allow for the passive diffusion of the esters through the cell membrane resulting in the liberation of the anionic dye by the action of cytosolic esterases, R. Y. Tsien, "A non-disruptive technique for loading calcium buffers into cells, Nature, 290, 527–528 (1981).

Chlorin $e_6$ and pheophorbide a are chlorins which are known to exhibit significant photocytotoxic activity, L. C. Bergstrom, I. Vucenik, S. Chernomorsky and R. D. Poretz, "Targeted photoactive immunoliposomes are cytotoxic to human bladder carcinoma cells," FASEB J., 5, A1558, (1991); J. D. Spikes, "Chlorins as photosensitizers in biology and medicine," J. Photochem. Photobiol. B. Biol., 6, 259–274 (1990); S. A. Chernomorsky, R. D. Poretz and A. B. Segelman, "The photodynamic effect of chlorophyll derivatives on murine myeloma cells in tissue culture," Photochem Photobiol., 39, 49S (1984); A. B. Segelman, I. K. Hagen, S. A. Chernomorsky, K. Weadock and G. H. Sigel, Jr., "Highly purified pheophorbide a as a photosensitizer in human bladder cancer in vitro," New Directions of Photodynamic Therapy, (Edited by D. C. Neckers), pp. 205–209, SPIE (1987); G. A. Kostenich, I. N. Zhuravkin, A. V. Furmanchuk and E. A. Zhavrid, "Photodynamic therapy with chlorin $e_6$. A morphologic study of tumor damage efficiency in experiment," J. Photochem. Photobiol. B. Biol., 11, 307–318 (1991); G. A. Kostenich, I. N. Zhuravkin, A. V. Furmanchuk and E. A. Zhavrid, "Sensitivity of different rat rumour strains to photodynamic treatment with chlorin $e_6$," J. Photochem. Photobiol. B. Biol., 17, 187–194 (1993).

The photocytotoxic effect of chlorin $e_6$ is known to be greatly enhanced when it is delivered to intracellular compartments by specific carriers, A. R. Oseroff, D. Ohuoha, T. Hasan, J. C. Bommer and M. L. Yarmush "Antibody targeted photolysis: selective photodestruction of human T-cell leukemia cells using monoclonal antibody-chlorin $e_6$ conjugates," Proc. Nat'l. Acad. Sci. USA, 83, 8744–8748 (1986); T. V. Akhlynina, P. V. Gulak, N. V. Serebryakova, A. A. Rosenkranz and A. S. Sobolev "Photodynamic action of concanavalin A-Chlorin $e_6$ conjugate on human fibroblasts," Byull. Eksp. Biol. Med., 109, 150–152 (1990); J. Kopecek, N. L. Krinick, B. Rihova and K. Ulbrich "Targetable N-(2-hydroxypropyl) methacrylamide copolymer-chlorin $e_6$ conjugates," *Photodynamic Therapy: Mechanisms II*, (Edited by T. J. Dogherty), pp. 144–152, SPIE, (1990); R. Bachor, C. R. Shea, S. J. Belmonte and T. Hasen "Free and conjugated chlorin $e_6$ in the photodynamic therapy of human bladder carcinoma cells," *J. Urol.*, 146, 1654–1658 (1991). R. Bachor, M. Scholz, C. R. Shea and T. Hasan, "Mechanism of photosensitization by microsphere-bound chlorin $e_6$ in human bladder carcinoma cells," *Cancer Res.*, 51, 4410–4414 (1991); A. S. Sobolev, T. V. Akhlynina, S. V. Yachmenev, A. A. Rosenkranz and E. S. Severin, "Internalizable insulin-BSA-chlorin $e_6$ conjugate is a more effective photosensitizer than chlorin $e_6$ alone," *Biochem. Int.*, 26, 445–450 (1992). This enhancement phenomenon apparently is due to the potential trianionic charge of the PS at neutral pH values, thereby resulting in a membrane-impermeable form, R. Pottier and J. C. Kennedy, "The possible role of ionic species in selective biodistribution of photochemotherapeutic agents toward neoplastic tissue," *J. Photochem. Photobiol. B. Biol.*, 8, 1–16 (1990).

ADVANTAGES AND SUMMARY OF THE INVENTION

The subject invention is directed to a method of preparation of a pH-sensitive amphipathic drug compound comprising converting a pH-sensitive amphipathic parent drug compound to a lipophilic derivative having a high lipophilicity and combining the derivative with a lipophilic carrier or other pharmaceutically acceptable agent that delivers the derivative to the lysosome of a target cell where the derivative is converted back to the pH-sensitive amphipathic parent compound by lysosomal esterases. After being converted back to the pH-sensitive amphipathic parent compound, the compound exits the lysosome and enters extralysosomal compartments where it may become pharmaceutically more beneficial.

In particular, the subject invention is directed to preparing lipophilic derivatives having a sufficiently high lipophilicity such that the lipophilic derivative may be combined with and remain bound to the lipophilic carrier without being substantially released until delivered to the lysosomes of the target cell. The subject invention will be illustrated herein in terms of delivering pH-sensitive amphipathic photosensitizers (PS) to target cells that are to be photocytotoxically destroyed by photodynamic therapy (PDT). However, the method disclosed herein is intended to be illustrative only and the full scope of the invention is directed to a method of preparation of a pharmaceutical composition comprising selecting a pH-sensitive amphipathic, parent compound, reacting the parent drug compound in a manner such as to convert it to a lipophilic derivative and combining the lipophilic derivative with a lipophilic carrier or other pharmaceutically acceptable agent to form a pharmaceutical composition, the lipophilic derivative being capable of being converted back to the parent compound by lysosomal enzymes in the cell.

An advantage of the subject invention is that it may be used to provide a lipophilic derivative of a pH-sensitive amphipathic compound that is capable of being preferentially delivered, by use of selected lipophilic carriers, to target cells without having the lipophilic derivative partitioning out of the lipophilic carrier into more hydrophilic compartments prior to delivery to the target cell.

A further advantage of the subject invention is that the lipophilic derivative can be converted back to its pharmaceutically beneficial, pH-sensitive amphipathic parent drug compound by lysosomal enzymes such that it may exit the lysosome and enter extralysosomal compartments of the cell.

A specific object of the subject invention is to provide acetoxymethyl esters of porphyrin-type compounds that may be used as photosensitizers in photodynamic therapy.

DETAILED DESCRIPTION OF THE PREFERRED EMBODIMENTS

The subject invention will now be described in detail for specific preferred embodiments of the invention, it being understood that these embodiments are intended as illustrative examples and the invention is not to be limited thereto.

The pH-sensitive amphipathic parent drug compound of the subject invention may be selected from a wide range of pharmaceutically acceptable compounds. Examples of such compounds include porphyrins, photosensitizers, taxane-like compounds, antimitotic agents and active-site-directed enzyme inhibitors. Such compounds may be used for a wide range of therapeutic purposes, including photodynamic therapy, anti-cancer therapy, atherosclerosis and cardiovascular therapy and anti-metabolite therapy. In the preferred illustrative embodiment of the subject invention, pH-sensitive amphipathic compounds that are useful as photosensitizers in photodynamic therapy are disclosed. In particular, the subject invention is demonstrated for the conversion of pH-sensitive amphipathic porphyrins, e.g., chlorin $e_6$ and pheophorbide a, to their lipophilic acetoxymethyl ester derivatives.

The chemical structures of the chlorin $e_6$ and pheophorbide a and their ester derivatives are shown below:

| | |
|---|---|
| Pheophorbide a: | $R_1-CO_2H$, $R_2-CO_2CH_3$ |
| Pheohporbide a methyl ester: | $R_1-R_2-CO_2CH_3$ |
| Pheophorbide a acetoxymethyl ester (PAME): | $R_1-CO_2CH_2O_2CH_3$, $R_2-CO_2CH_3$ |
| Pheophytin: | $R_1-CO_2C_{20}H_{39}$, $R_2-CO_2CH_3$ |

| | |
|---|---|
| Chlorin $e_6$: | $R_3-CO_2H$ |
| Chlorin $e_6$ acetoxymethyl triester (CAME): | $R_3-CO_2CH_2O_2CCH_3$ |

Both chlorin $e_6$ and pheophorbide a possess free carboxylic acid groups that contribute to the functioning of these parent compounds as pH-sensitive amphipathic compounds. The term "parent compound", as used herein, is understood to mean any compound that can be converted into a derivative of that compound and subsequently converted back to the parent compound. As shown, the ester derivatives that were prepared include pheophorbide a methyl ester, pheophorbide a acetoxymethyl ester (PAME), pheophytin and chlorin $e_6$ acetoxymethyl triester (CAME). Details of the preparation and characterization of these esterified porphyrins are described in Example 1, 1A and 1B, respectively.

Figure 1:
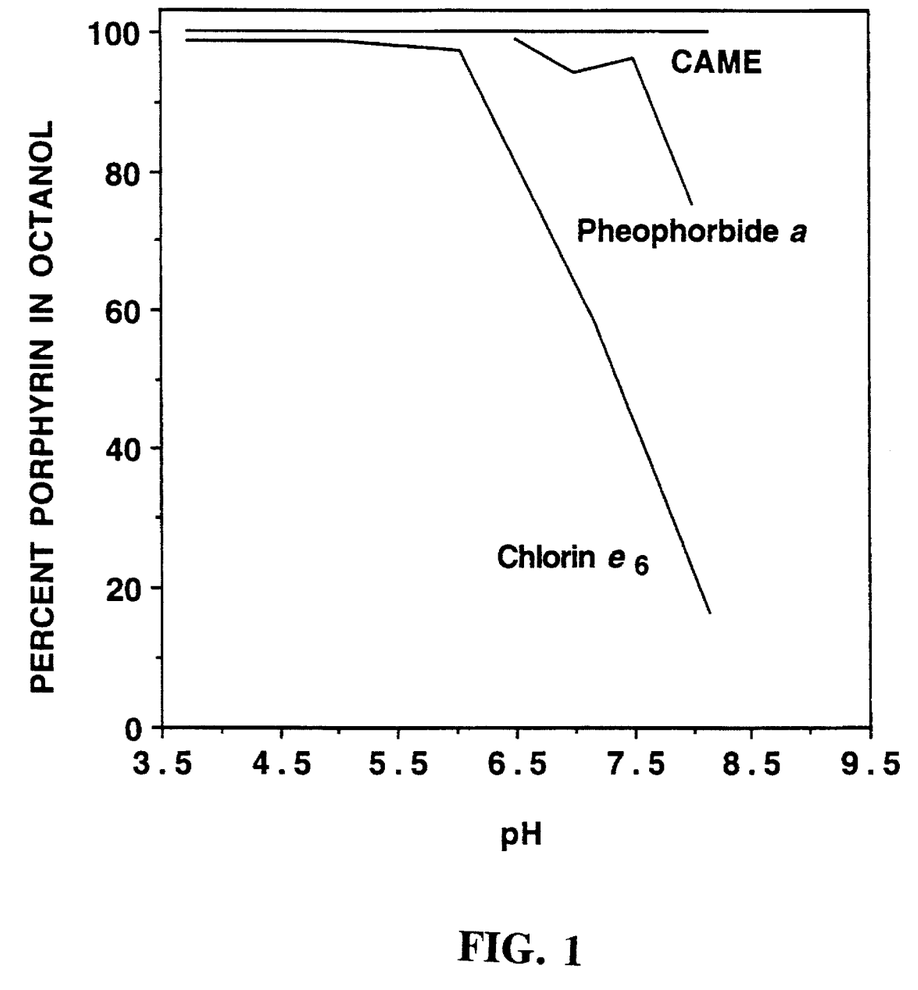
FIG. 1 shows the partitioning of chlorins between 1-octanol and water at different pH values, from D. Sahai, J- L. Lo, I. K. Hagen, L. Berstrom, S. Chernomorsky and R. D. Poretz, "Metabolically convertible lipophilic derivatives of pH-sensitive amphipathic photosensitizers," *Photochem. and Photobiol.*, 58, pp.803–808 (1993).

The lipophilicity of a compound may be expressed in terms of an octanol:water partition ratio that may be determined by introducing the compound into a mixture of equal volumes of 1-octanol and aqueous buffer and then determining the relative amount of the compound that partitions into each phase of the mixture at equilibrium. The partitioning properties of the chlorins between 1-octanol and various aqueous buffers demonstrated that both chlorin $e_6$ and pheophorbide a are pH-sensitive amphipathic compounds (FIG. 1). Both chlorins exhibit intense lipophilicity, and thus, hydrophobicity, at pH values below about 6.5, and increasing hydrophilicity at values beyond neutrality, above about pH 7. Chlorin $e_6$, of which nearly 100% partitions into the organic phase at a pH below about pH 6.0, exhibits a strong tendency to enter the aqueous phase between about pH 7 to about pH 8. Pheophorbide a shows the same general pattern as chlorin $e_6$, but is significantly less hydrophilic at pH 7–8. Accordingly, chlorin $e_6$ exhibits the partitioning properties required for a compound to be lipophilic in the acidic milieu of the lysosome and, in addition, exhibits increased hydrophilicity in environments characteristic of cytosolic compartments of mammalian cells. The results in FIG. 1 show that pheophorbide a, while exhibiting increased hydrophilicity at higher pH, appears to be less desirable than chlorin $e_6$ in this regard.

As shown in FIG. 1, esterification of the carboxylic acid groups of chlorin $e_6$ results in a compound that remains highly lipophilic throughout the pH range studied. Substantially 100% of the chlorin $e_6$ triacetoxymethyl ester partitions into the 1-octanol phase between pH 3.7 and 8.2. Furthermore, triesterification of chlorin $e_6$ by potentially labile acetoxymethyl groups produces a derivative that would be expected to remain hydrophobic in all intra- and extra-cellular compartments.

While the preferred embodiments of the subject invention are directed to lipophilic derivatives that may be prepared by esterifying a pH-sensitive amphipathic drug compound such as to obtain a lipophilic derivative having high lipophilicity, other methods known to one skilled in the art may be used to convert the pH-sensitive amphipathic compound into a lipophilic derivative. In particular, any type of reaction that involves reacting a pH-sensitive amphipathic drug compound to convert it to a lipophilic derivative having the desired lipophilicity is intended to be included within the scope of the subject invention. In particular, a lipophilic derivative of the subject invention may have an octanol:water partition ratio of at least about 80:20, more preferably, at least about 90:10, and most preferably, at least about 99:1 over the pH range from about pH 3 to about pH 8.5.

The pH-sensitive amphipathic parent compound is substantially lipophilic at pH levels less than about 5 and substantially hydrophilic at pH levels above about 6. More specifically, the pH-sensitive amphipathic parent compound preferably has an octanol:water partitioning ratio of at least about 80:20 at pH levels less than about pH 6.0 and an octanol:water partitioning ratio of less than about 70:30 at pH levels higher than about pH 8.0.

While the results disclosed herein are intended to show that the specific pH-sensitive amphipathic porphyrins chlorin $e_6$ and pheophorbide a can be converted into lipophilic compounds, other pH-sensitive amphipathic compounds that can be converted into highly lipophilic derivatives also fall within the scope of the subject invention. In particular, lipophilic derivatives of pH-sensitive amphipathic compounds that fall within the scope of the subject invention are those that can be prepared with sufficient lipophilicity such that the lipophilic derivative may be combined with a lipophilic carrier for delivery to specific target cells without substantial partitioning of the lipophilic derivative out of the lipophilic carrier into more hydrophobic compartments prior to delivery into the target cells.

The lipophilic carrier may be selected from a large number of known carriers, such as liposomes, immunoliposomes, lipoproteins and other pharmaceutically acceptable carriers. The preferred lipophilic carrier of the subject invention that may be used with the lipophilic derivatives disclosed herein is LDL (low density lipoprotein) as described, for example, in F. N. Jiang, B. Allison, D. Liu and J. G. Levy, "Enhanced photodynamic killing of target cells by either monoclonal-antibody or low-density-lipoprotein mediated delivery systems," Controll. Release, 19, 41–58 (1992). However, the lipophilic derivative may be combined with other lipophilic carriers known in the art while still remaining within the scope of the present invention.

The subject invention is further directed to lipophilic carriers that may be preferentially targeted to cells and be taken up by endocytosis such that the lipophilic derivative may then be converted in the lysosomes back into the pharmaceutically beneficial pH-sensitive amphipathic parent compound. Examples of the lipophilic carriers that may be selected in accordance with their specificity to be taken up by particular target cells include high density lipoprotein, oxidized LDL, immunoliposomes and LDL, which may be selected so as to target liver cells, foam cells, specific cancers and many types of cancers, respectively.

The subject invention is directed at providing lipophilic derivatives that can be associated with lipophilic carriers in a manner such that they remain substantially carrier-associated until preferentially delivered to lysosomes in target cells for conversion back to the pharmaceutically beneficial parent compound. The preferred embodiment of the subject invention involves a combination of the lipophilic derivative, for example, CAME, with a lipophilic carrier such as LDL, as described in Example 2. Experiment II shows that the esterified CAME-LDL may be selectively delivered to the lysosomes of target human bladder tumor cells MGH-U1 that were grown in vitro.

Experiment III shows that the preferred lipophilic derivatives of the subject invention, the chlorin $e_6$ and pheophorbide a acetoxymethyl esters, may be converted by lysosomal esterases back to the (free-acid-containing) pH-sensitive amphipathic parent compounds that are pharmaceutically beneficial. The results of Experiment III further show that other esters, such as the methyl ester of pheophorbide a and pheophytin a and b, were not converted back to the pH-sensitive amphipathic, free-acid form.

Experiment IV shows that CAME-LDL is photocytotoxic to human bladder tumor cells. One skilled in the art would recognize that the experiments, when taken as a whole, are consistent with the notion that the lipophilic derivative had been internalized into the lysosomes and converted back into the parent compound by lysosomal enzymes to yield the pharmaceutically more beneficial, pH-sensitive amphipathic parent compound that then migrates out of the lysosome into the cytosol.

This invention will now be described in detail with respect to the specific preferred embodiments thereof, the materials and the process steps of the following it being understood that examples are intended to be illustrative only. The invention is not intended to be limited to the materials, conditions, process parameters and the like recited herein.

EXAMPLES OF THE PREFERRED EMBODIMENTS

Example 1

A. Preparation of the Lipophilic Derivatives

For the preparation of chlorin $e_6$ triacetoxymethyl ester (CAME), 6 µl (60 µmol) of bromomethyl acetate (Aldrich Chemical Co., Milwaukee, Wis.) and 5 µl (30 µmol) of N,N"-diisopropylethylamine (Aldrich Chemical Co.) were added to 1 ml of a stirred solution of chlorin $e_6$ (6 mg, 10 µmol, Porphyrin Products, Logan, Utah) in acetonitrile, kept under $N_2$ at room temperature. The reaction was monitored by thin-layer chromatography (TLC) on fluorescent $C_8$ reverse-phase silica plates developed with methanol/acetone/toluene (29:41:1.5 vol/vol/vol) and detected by UV illumination, as well as by high-performance liquid chromatography (HPLC) using a $C_{18}$ reverse-phase silica column (4.6×250 mm) eluted with a gradient from methanol/1M ammonium acetate (80:20 vol/vol) to methanol/acetone (80:20 vol/vol) and detection by absorption of light at 408 nm, essentially as described in M. Zapata, A. M. Ayala, J. M. Franco and J. L. Garrido, "Separartion of chlorophylis and their degradation products in marine phytoplankton by reversed-phase high-performance liquid chromatography," *Chromatographia*, 23, 26–30 (1987). During the time course of the reaction, the chlorin $e_6$ decreased in quantity and more apolar products appeared. After 23 hours, the reaction mixture was partitioned between water and toluene. The organic layer was separated, dried over anhydrous sodium sulfate and evaporated to dryness in vacuo. The residue was dissolved in acetone and CAME, which was produced in 70% yield, was purified by HPLC as described above with a 90% recovery. Analytical HPLC of this material indicated a purity of 94%. The impurities that absorbed light at 408 nm consisted predominantly of putative partial esters of chlorin $e_6$ and less than 1% starting material. Alternatively, a 20 hour reaction mixture was dissolved in toluene and extracted twice with 0.1M sodium phosphate buffer, pH 7.6, followed by water washes. The toluene layer was separated, dried over anhydrous sodium sulfate and evaporated to dryness in vacuo. This process resulted in an 80% overall yield of CAME with a purity of 85%.

Pheophorbide a acetoxymethyl ester (PAME) was prepared in a manner analogous to that described for CAME but employing pheophorbide a (Porphyrin Products) in place of chlorin $e_6$. Purification by HPLC yielded material that by absorption of light at 408 nm was 87% PAME, 3% pheophorbide a and 10% unidentifiable material.

Methyl pheophorbide a and pheophytin a+b were prepared as described in G. W. Kenner, S. W. McCombie and K. M. Smith, "Pyrroles and related compounds. Part XXIV. Separation and oxidative degradation of chlorophyll derivatives," *J. C. S. Perkin I*, 2517–23 (1973) and J. H. Furhop and K. M. Smith, "Laboratory methods," *Porphyrins and Metalloporphyrins*, (Edited by K. M. Smith), Elsevier, Amsterdam, pp. 774–775 (1975), respectively.

B. Characterization of the Lipophilic Derivatives

An HPLC analysis of the acetoxymethyl esterification of the chlorin $e_6$ reaction mixture demonstrated that the products exhibit mobilities indicating that each is more hydrophobic than the starting chlorin. Increased esterification reaction times resulted in increased production of CAME and decreased amounts of the starting material. Preparative HPLC allowed for the isolation of CAME in 94% purity. As would be expected for CAME, treatment with HCl resulted in destruction of the triester and production of chlorin $e_6$. Though the nature of the other products that were produced was not studied further, the partial HCl hydrolysis of CAME yielded material that corresponded to these components, suggesting that they may represent isomeric forms of the mono-and diesters of chlorin $e_6$. Mass spectral analysis of the material identified as CAME was consistent with the molecular ion and fragmentation pattern that would be expected for CAME. The visible absorption spectra of CAME and chlorin $e_6$ in 1,4-dioxane are virtually identical with $\epsilon_{402}$=160.7×$10^3 M^{-1}$ and $\epsilon_{667}$=53.5×$10^3 M^{-1} cm^{-1}$ for CAME, as compared to 149.3×$10^3 M^{-1} cm^{-1}$ and 52.6× $10^3 M^{-1} cm^{-1}$, respectively, for chlorin $e_6$. The fluorescence excitation and emission spectra of CAME in 1,4-dioxane are identical to those of chlorin $e_6$. The proton NMR analysis of CAME in deuterochloroform at 500 MHz yielded the following chemical shift and chemical coupling constants expressed as ppm and Hz, respectively: 9.64, 9.47, 8.66 (each s, 1H, β, α, δ -H); 8.01 (dd, 1H, 2-CH=$CH_2$, $J_{cis}$=11 Hz, $J_{trans}$=18 Hz); 6.30 (dd, 1H, 2-CH=$CH_2$, $J_{trans}$=18 Hz, $J_{gem}$=2 Hz); 6.12 (d, 1H, 2-CH=$CH_2$, J=11 Hz); 6.31 (2H, 6-$CO_2CH_2O_2CCH_3$); 5.85 (2H, γ-$CO_2CH_2O_2CCH_3$); 5.65 (2H, 7-$CO_2CH_2O_2CCH_3$); 5.31 (d, 2H, γ-$CH_2$, J=18 Hz); 2.55 and 2.14 (each m, 2H, 7-$CH_2CH_2$); 4.39 (m, 8-H); 4.38 (q, 7-H); 3.55 (s, 3H, 5-$CH_3$); 3.43 (s, 3H, 1-$CH_3$); 3.25 (s, 3H, 3-$CH_3$); 3.73 (q, 2H, 4-$CH_2CH_3$); 1.68 (t, 3H, 4-$CH_2CH_3$); 1.73 (d, 3H, 8-$CH_3$, J=7 Hz); −1.10 and −1.21 (each s, 1H, 2 NH).

Pheophorbide a acetoxymethyl ester (PAME) was obtained in 87% purity by preparative HPLC. As observed for CAME, PAME exhibited a longer retention time on reverse-phase HPLC than its parent chlorin, and acid hydrolysis of PAME yielded pheophorbide a. The FAB/LSIMS analysis of the purified PAME yielded a spectrum consistent with that expected for the acetoxymethyl ester of pheophorbide a. No further analysis was performed on this material.

Example 2

Preparation of CAME-LDL

To 1 ml of McCoy's medium lacking serum and containing 0.1% bovine serum albumin (M-BSA), 220 µg of CAME in 100 µl of dimethylsulfoxide is combined with LDL (500 µg of LDL protein) in 100 µl of 0.5M TRIS-HCl buffer, pH 7.4, containing 0.15M NaCl and 0.3M ethylenediaminetetraacetic acid. After 15 minutes, the preparation is diluted to 5 ml with M-BSA and incubated at 4° C. overnight. Density equilibrium centrifugation experiments demonstrated that at these concentrations of CAME and LDL, all the CAME associated with the LDL.

Experiment I

Lipophilicity Measurements

Octanol:water partition ratios for pheophorbide a, chlorin $e_6$ and CAME were obtained for 1-octanol/aqueous buffer systems as described above. Appropriate buffers were saturated with 1-octanol and in turn, 1-octanol was saturated with each buffer employed. One milliliter of each 1-octanol phase containing the chlorin (2 µg/ml) was mixed vigorously and continuously with an equal volume of the respective buffer phase at 20° C. for 20 hours. The phases were separated following centrifugation at 800 g for 20 minutes and the chlorin content was determined by fluorescence (pheophorbide a, $\lambda_{ex}$=416 nm, $\lambda_{em}$=678 nm; CAME and chlorin $e_6$, $\lambda_{ex}$=402 nm, $\lambda_{em}$=667 nm). Pheophorbide a octanol:water partition-ratio experiments were performed with 0.05M HEPES/HCl buffers, pH 6.5, 7.0, 7.5 and 8.0. Similar results were obtained when phosphate or barbital buffers were employed in this pH range. Slight differences in ionic strength among the different buffers as well as at different pH values may be expected to have some influence on the results of the octanol:water partition experiments with pheophorbide a. Partition experiments with CAME and chlorin $e_6$ employing the constant ionic strength universal buffer, citrate/phosphate/KCl (I=0.55) at pH 3.7, 5.0, 6.0, 7.2 and 8.2 produced similar partition ratio values.

Experiment II

Sub-cellular Localization of CAME-LDL

Step 1

Human bladder tumor cells MGH-U1 were grown in vitro in a 150 cm² flask for 36 hours in McCoy's medium lacking serum and containing 0.1% bovine serum albumin (M-BSA). The cells were treated with CAME-LDL (70 µg of LDL protein and 18 nm of CAME) in 7 ml of M-BSA for 90 minutes. Following treatment, the cells were washed with medium and fractionated by sediment-velocity centrifugation as described by L. C. Bergstrom, I. Vucenik, I. K. Hagen, S. A. Chernomorsky and R. D. Poretz, *J. Photochem, Photobiol.*, in press (1994). Analysis of the subcellular fractions by fluorescence for CAME and β-hexosaminidase activity for localization of the lysosomal fraction demonstrated that 88% of the CAME (or its de-esterified products) present in the post-nuclear fraction was localized in the lysosome/mitochondrial fraction. Only 12% or less was found in the cytosol/Golgi fraction:

| Fraction of CAME in: | |
| --- | --- |
| Lysosomes/mitochondria | 88% |
| Cytosol/Golgi | 12% |

Step 2

Cells were treated in a manner identical to that described in Step 1. The post nuclear supernatant was fractionated by Percoll density fractionation as described in R. D. Poretz, I. Vucenik, L. Bergstrom, A. Segelman, G. Sigel Jr. and S. A. Chernomorsky, SPIE 1065, 97–203 (1989). Over 54% of the CAME (or its de-esterified products) was localized in whole lysosomes or within the fraction containing membranes from broken lysosomes. No CAME was detected in the fractions corresponding to mitochondria. Only 18% was found in the cytosol. All of the cytosolic CAME (or its de-esterified products) can be accounted for as being derived from broken lysosomes. The lysosomes are presumed to have broken during the preparation of the post nuclear supernatant.

| Fraction of CAME in: | |
| --- | --- |
| Lysosomes/lysosome derived | 72% |
| Mitochondria | 0% |
| Other (including endosomes) | 28% |

Experiment III

De-esterification by the Lysosomes

To examine the ability of PAME and CAME to serve as substrates for lysosomal esterases and to compare these to the naturally occurring phytyl esters of pheophorbide a, pheophytin a and b, and to pheophorbide a methyl ester, these compounds were incubated at pH 4.8 with lysosomal enzymes isolated from MGH-U1 human bladder tumor cells. Incubations contained 13 nmol of chlorin and either 75 µl or 100 µl of the lysosome suspension (equivalent to $2.2 \times 10^5$ or $6.0 \times 10^5$ cells) in a total volume of 150 or 175 µl for the shorter or longer incubation periods, respectively. In addition, the reactions contained 0.25% Triton X-100, 0.05M acetate buffer, pH 4.8, and 0.1% bovine serum albumin (which was used to decrease potential nonspecific adsorption of lysosomal enzymes). Control incubations were performed in an identical manner but lacked the lysosomal enzymes.

Following incubation at 37° C. for 20 or 48 hours, the suspensions were mixed with five parts of cold acetone and centrifuged to remove proteinaceous material. The supernatants were dried in vacuo and dissolved in acetone. The HPLC analysis, as described supra, was performed to determine the nature and quantity of each chlorin.

As shown in Table 1, incubation of PAME with a mixture of lysosomal enzymes for 20 h at 37° C. resulted in a 34% [1-(57/87)×100] conversion of the ester to pheophorbide a. The de-esterification of CAME is more complex, resulting in the potential production of the putative mono- and diacetoxyl-methyl esters as well as free chlorin $e_6$. Table 1 shows that with 20 h incubation, over 40% of the CAME is partially de-esterified, producing appreciable amounts of the mono-and di-esters, but with only marginal amounts of chlorin $e_6$. Longer incubation times of 48 h, however, clearly demonstrate that lysosomal enzymes act on over 81% of the CAME and are capable of removing all three ester groups to yield significant amounts of the free chlorin. In contrast to the complex acetoxymethyl esters of the chlorin, simple esters of pheophorbide a, which upon hydrolysis yield methanol or phytol, are not acted upon by the lysosomal enzymes, under the conditions employed here.

Experiment IV

CAME-LDL Photocytotoxicity

In order to demonstrate that CAME-LDL is photocytotoxic to human bladder tumor cells in vitro, MGH-Ul cells were grown in vitro in M-BSA for 36 hours and exposed to CAME-LDL (70 µg of LDL protein containing either 18 nm or 1.8 nm of CAME) in 7 ml of M-BSA. After 40 minutes the treatment medium was removed and the cells were washed with medium and fresh medium was added. Cells were exposed to white light for various periods of time. Cells were then further incubated in the dark for 8 days. Thereafter, the cells were harvested and counted in the presence of trypan blue dye to show which cells were viable. The number of viable cells was determined relative to those in the control samples treated identically but not exposed to light.

Figure 2:
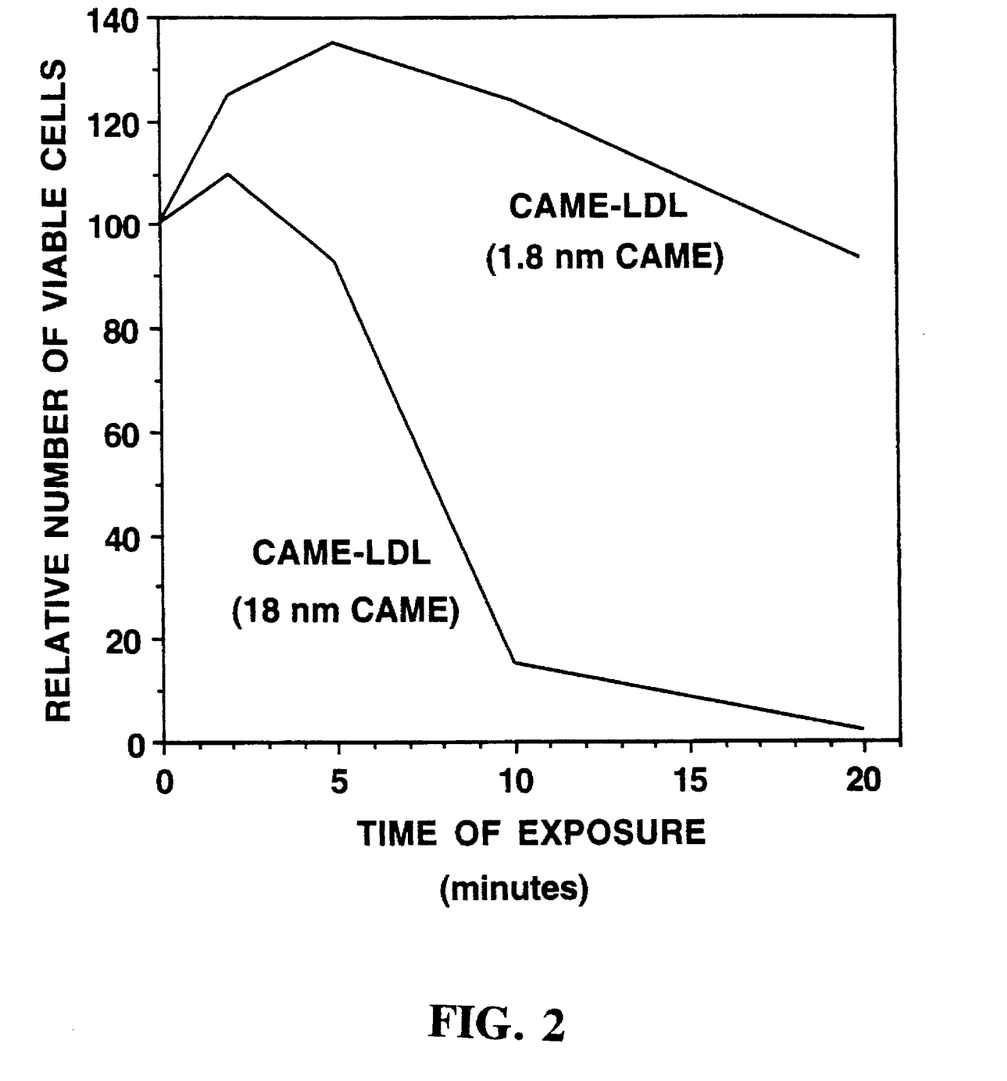
FIG. 2 shows the effect of light exposure or amount of phototoxic agent on the viability of cells in samples containing lysosomes to which a lipophilic, pH-insensitive derivative is delivered. The lipophilic, pH-insensitive, derivative is disclosed herein to be susceptible to lysosomal conversion to its pharmaceutically more beneficial, pH-sensitive amphipathic form.

FIG. 2 shows the effect of light exposure or amount of photoactive agent on the number of viable cells present in the experimentally treated samples relative to the number in control sample not exposed to light. The amount of light and the amount of photoactive agent present in the CAME-LDL impact on the degree to which cells are affected.

TABLE 1

Potential of pheophorbide a and chlorin $e_6$ esters to serve as substrates for lysosomal esterases

| Chlorin | Percent of compound in total recovered chlorin | | |
| --- | --- | --- | --- |
| | Original ester | Partial Esters* | Free Acid |
| PAME (no enzyme) | 87 | 10 | 3 |
| PAME | 57 | 11 | 32 |
| CAME (no enzyme) | 94 | 5 | <1 |
| CAME (condition)† | 56 | 43 | <1 |
| CAME (condition)‡ | 18 | 73 | 9 |
| Pheophorbide a methyl ester (no enzyme) | 90 | 9 | <1 |
| Pheophorbide a methyl ester | 89 | 10 | <1 |
| Pheophytin a and b (no enzyme) | 82 | 17 | <1 |
| Pheophytin a and b | 76 | 24 | <1 |

*Partial esters of CAME or unidentifiable components of PAME, pheophorbide a methyl ester or pheophytin a and b, respectively.
†Lysosomal enzymes from $2.2 \times 10^5$ cells in a total reaction volume of 150 µl and an incubation time period of 20 h.
‡Lysosomal enzymes from $6.0 \times 10^5$ cells in a total reaction volume of 175 µl and an incubation time period of 48 h.

What is claimed is:

1. A method of preparation of a pharmaceutical composition comprising:

selecting a pH-sensitive amphipathic parent drug compound, said parent drug compound having an octanol:water partitioning ratio of at least about 80:20 at pH levels less than about pH 6.0 and an octanol:water partitioning ratio of less than about 70:30 at pH levels higher than about pH 8.0;

converting the parent drug compound to a lipophilic derivative of said parent drug compound, said lipophilic derivative having an octanol:water partitioning ratio of at least about 80:20 at a pH of about 3 to a pH of about 8.5; and then combining the lipophilic derivative with a lipophilic carrier to form a pharmaceutical composition, the lipophilic derivative being capable of being converted back to the parent drug compound by lysosomal enzymes.

2. The method according to claim 1 wherein said lipophilic derivative has a sufficiently high lipophilicity such that the lipophilic carrier is capable of delivering the lipophilic derivative to the lysosome of a cell without substantial partitioning of the lipophilic derivative out of the lipophilic carrier prior to delivery to a cell.

3. The method according to claim 1 wherein said pH-sensitive amphipathic parent compound is substantially lipophilic at pH levels less than about 5 and substantially hydrophilic at pH levels above about 6.

4. The method according to claim 1 said lipophilic derivative has an octanol:water partitioning ratio of at least about 90:10 at a pH of about 3 to a pH of about 8.5.

5. The method according to claim 4 wherein said lipophilic derivative has an octanol:water partitioning ratio of at least about 99:1 at a pH of about 3 to a pH of about 8.5.

6. The method according to claim 1 wherein said lipophilic carrier is selected from the group consisting of lipoproteins, liposomes and immunoliposomes.

7. The method according to claim 1 wherein said parent drug compound is a porphyrin.

8. The method according to claim 7 wherein said porphyrin is a chlorin.

9. The method according to claim 8 wherein said chlorin is selected from the group consisting of chlorin $e_6$ and pheophorbide a.

10. The method according to claim 1 wherein said lipophilic derivative is an ester of said parent drug compound.

11. The method according to claim 10 wherein said lipophilic derivative is an acetoxymethyl ester of said parent drug compound.

12. The method according to claim 1 wherein the converting step comprises esterifying said parent drug compound.

13. A pharmaceutical composition comprising:

a lipophilic derivative of a pH-sensitive amphipathic parent drug compound, said parent drug compound having an octanol:water partitioning ratio of at least about 80:20 at pH levels less than about pH 6.0 and an octanol:water partitioning ratio of less than about 70:30 at pH levels higher than about pH 8.0, said lipophilic derivative having an octanol:water partitioning ratio of at least about 80:20 at a pH of about 3 to a pH of about 8.5, said lipophilic derivative being combined with a lipophilic carrier and said lipophilic derivative being capable of being converted to the parent drug compound by lysosomal enzymes.

14. The pharmaceutical composition of claim 13 wherein said pH-sensitive amphipathic parent drug compound is a photocytotoxic compound.

15. The pharmaceutical composition of claim 14 wherein said photocytotoxic compound is a porphyrin.

16. The pharmaceutical composition of claim 15 wherein said porphyrin is a chlorin.

17. The pharmaceutical composition of claim 16 wherein said chlorin is selected from the group consisting of chlorin $e_6$ and pheophorbide a.

18. The pharmaceutical composition of claim 11 wherein said lipophilic derivative is an ester of said photocytotoxic compound.

19. The pharmaceutical composition of claim 18 wherein said lipophilic derivative is an acetoxymethyl ester of said photocytotoxic compound.

20. The pharmaceutical composition of claim 13 wherein said lipophilic derivative has an octanol:water partitioning ratio of at least about 90:10 at a pH of about 3 to a pH of about 8.5.

21. The pharmaceutical composition of claim 20 wherein said lipophilic derivative has an octanol:water partitioning ratio of at least about 99:1 at a pH of about 3 to a pH of about 8.5.

22. The pharmaceutical composition of claim 13 wherein said lipophilic derivative is an ester of said parent drug compound.

23. The pharmaceutical composition of claim 13 wherein said lipophilic derivative is an acetoxymethyl ester of said parent drug compound.

24. A drug compound comprising:
a lipophilic derivative of a pH-sensitive amphipathic parent compound, said parent compound having an octanol:water partitioning ratio of at least about 80:20 at pH levels less than about pH 6.0 and an octanol:water partitioning ratio of less than about 70:30 at pH levels higher than about pH 8.0 and said lipophilic derivative having an octanol:water partitioning ratio of at least about 80:20 at a pH of about 3 to a pH of about 8.5 and being capable of being converted to the parent compound by lysosomal enzymes.

25. The drug compound of claim 24 wherein said lipophilic derivative has an octanol:water partitioning ratio of at least about 90:10 at a pH of about 3 to a pH of about 8.5.

26. The drug compound of claim 25 wherein said lipophilic derivative has an octanol:water partitioning ratio of at least about 99:1 at a pH of about 3 to a pH of about 8.5.

27. The drug compound of claim 24 wherein said parent drug compound is a porphyrin.

28. The drug compound of claim 27 wherein said porphyrin is a chlorin.

29. The drug compound of claim 28 wherein said chlorin is selected from the group consisting of chlorin $e_6$ and pheophorbide a.

30. The drug compound of claim 29 wherein said lipophilic derivative is an ester of said chlorin.

31. The drug compound of claim 30 wherein said lipophilic derivative is an acetoxymethyl ester of said chlorin.

* * * * *

UNITED STATES PATENT AND TRADEMARK OFFICE
CERTIFICATE OF CORRECTION

PATENT NO.  : 5,599,831
DATED       : February 4, 1997
INVENTOR(S) : Ronald D. Poretz It is certified that error appears in the above-indentified patent and that said Letters Patent is hereby corrected as shown below:

On the title page, second column, lines 2-4, delete "H. Ferres, Pro-drugs of $\beta$-lactam antibiotics, Chem. Ind., 435-440 (1980)".

On the face of the patent, second column, line 6, after "cells", delete " ", " and substitute therefore --,"--.

On the face of the patent, second column, line 8, after "bide" delete "$\alpha$" and substitute therefore -- a --.

On the face of the patent, second column, line 9, after "therapy", delete " ", " and substitute therefore --,"--.

Page 2, first column, line 7, delete "$\alpha$" and substitute therefore -- a --.

Page 2, first column, line 9, after "Neckers)," delete "pp.".

Page 2, first column, line 29, delete "Hasen" and substitute therefore --Hasan--.

Page 2, second column, line 21, after "2517-", delete "23" and substitute therefore --2523--.

Page 2, second column, line 29, after "1065,", delete "97" and substitute therefore --197--.

Column 2, line 55, first word, change "rumor" to --tumor--.

Column 3, line 5, delete "Hasen" and substitute therefore "Hasan".

Column 7, line 63, delete "chlorophylis" and substitute therefore --chlorophylls--.

UNITED STATES PATENT AND TRADEMARK OFFICE
CERTIFICATE OF CORRECTION

PATENT NO. : 5,599,831
DATED : February 4, 1997
INVENTOR(S) : Ronald D. Poretz

It is certified that error appears in the above-indentified patent and that said Letters Patent is hereby corrected as shown below:

Column 12, line 19, after "claim 1" insert --wherein--.

Signed and Sealed this

Twenty-eighth Day of October, 1997

Attest:

BRUCE LEHMAN

Attesting Officer

Commissioner of Patents and Trademarks